(12) United States Patent
Garino

(10) Patent No.: US 12,611,310 B2
(45) Date of Patent: *Apr. 28, 2026

(54) MODULAR ARTIFICIAL KNEE SYSTEM

(71) Applicant: Jonathan P. Garino, Villanova, PA (US)

(72) Inventor: Jonathan P. Garino, Villanova, PA (US)

( * ) Notice: Subject to any disclaimer, the term of this patent is extended or adjusted under 35 U.S.C. 154(b) by 949 days.

This patent is subject to a terminal disclaimer.

(21) Appl. No.: 17/868,971

(22) Filed: Jul. 20, 2022

(65) Prior Publication Data

US 2022/0354657 A1 Nov. 10, 2022

Related U.S. Application Data

(63) Continuation of application No. 17/167,194, filed on Feb. 4, 2021, now Pat. No. 11,419,731.

(51) Int. Cl.
*A61F 2/38* (2006.01)
*A61F 2/30* (2006.01)

(52) U.S. Cl.
CPC .......... *A61F 2/3868* (2013.01); *A61F 2/3836* (2013.01); *A61F 2/3859* (2013.01);
(Continued)

(58) Field of Classification Search
CPC .................................................... A61F 2/3886
See application file for complete search history.

(56) References Cited

U.S. PATENT DOCUMENTS 3,969,773 A    7/1976  Menschik
5,011,496 A    4/1991  Forte et al.
        (Continued)

FOREIGN PATENT DOCUMENTS

CN    109528362 A    3/2019
DE    69305434 T2    11/1997
        (Continued)

OTHER PUBLICATIONS

Office Action (The First Office Action) issued May 8, 2024, by the State Intellectual Property Office of People's Republic of China in corresponding Chinese Patent Application No. 201910783633.7 and an English translation of the Office Action (21 pages).
(Continued)

*Primary Examiner* — Megan Y Wolf
(74) *Attorney, Agent, or Firm* — Buchanan Ingersoll & Rooney PC

(57) ABSTRACT

A modular knee joint prosthesis is configured to move between an extended position and a flexion position. The modular knee joint prosthesis includes a femoral component that is configured to be mounted to a femur. The femoral component has a first cutout or opening in a central region thereof for receiving a femoral insert. The modular knee joint prosthesis also includes a tibial component that is configured to (i) be mounted either directly or indirectly to a tibia, and (ii) engage the femoral component. The tibial component has a second cutout or opening in a central region thereof for receiving a tibial insert. A kit includes the modular knee joint prosthesis, at least two of the femoral inserts having different geometries, and at least two of the tibial inserts having different geometries.

8 Claims, 18 Drawing Sheets

(52) U.S. Cl.

CPC .. *A61F 2/3886* (2013.01); *A61F 2002/30383* (2013.01); *A61F 2002/30523* (2013.01); *A61F 2002/30604* (2013.01); *A61F 2002/30607* (2013.01)

(56) References Cited

U.S. PATENT DOCUMENTS

| | | | |
|---|---|---|---|
| 5,871,543 A | 2/1999 | Hofmann | |
| 5,935,133 A | 8/1999 | Wagner et al. | |
| 6,325,828 B1 | 12/2001 | Dennis et al. | |
| 6,517,504 B1 | 2/2003 | Postelmans | |
| 6,629,999 B1 | 10/2003 | Serafin | |
| 6,660,039 B1 | 12/2003 | Evans et al. | |
| 6,905,513 B1 | 6/2005 | Metzger | |
| 8,409,293 B1 | 4/2013 | Howard et al. | |
| 8,480,752 B2 | 7/2013 | Dun | |
| 8,858,207 B2 | 10/2014 | Evans | |
| 9,387,084 B2 | 7/2016 | Masini et al. | |
| 9,861,484 B2 | 1/2018 | Sanford et al. | |
| 9,861,489 B2 | 1/2018 | Siebel | |
| 10,292,826 B2 | 5/2019 | Wyss et al. | |
| 10,682,236 B2 | 6/2020 | Boettiger | |
| 11,419,731 B1* | 8/2022 | Garino | A61F 2/3859 |
| 2003/0199985 A1 | 10/2003 | Masini | |
| 2004/0002767 A1* | 1/2004 | Wyss | A61F 2/3886 623/20.29 |
| 2005/0187635 A1 | 8/2005 | Metzger | |
| 2005/0209702 A1 | 9/2005 | Todd et al. | |
| 2009/0326668 A1 | 12/2009 | Dun | |
| 2010/0016979 A1 | 1/2010 | Wyss et al. | |
| 2010/0174378 A1* | 7/2010 | Metzger | A61F 2/30721 623/20.28 |
| 2012/0095563 A1 | 4/2012 | Sanford et al. | |
| 2012/0221113 A1 | 8/2012 | Katrana et al. | |
| 2014/0052265 A1 | 2/2014 | Slocum, Jr. et al. | |
| 2015/0182344 A1 | 7/2015 | McKinnon et al. | |
| 2015/0190236 A1 | 7/2015 | McMinn | |
| 2017/0252173 A1 | 9/2017 | Garino | |
| 2017/0333193 A1 | 11/2017 | Miura et al. | |
| 2018/0243100 A1 | 8/2018 | Boettiger | |
| 2018/0325681 A1 | 11/2018 | Lee et al. | |
| 2019/0029830 A1 | 1/2019 | Nguyen et al. | |
| 2019/0029847 A1 | 1/2019 | Nguyen et al. | |
| 2019/0091030 A1* | 3/2019 | Incavo | A61F 2/384 |
| 2019/0336297 A1* | 11/2019 | Reeder | A61F 2/3859 |
| 2020/0281732 A1 | 9/2020 | Garino | |
| 2021/0007855 A1 | 1/2021 | Collazo et al. | |
| 2022/0183856 A1 | 6/2022 | Mahfouz | |
| 2022/0241081 A1 | 8/2022 | Garino | |
| 2022/0354657 A1 | 11/2022 | Garino | |
| 2024/0173138 A1 | 5/2024 | Garino | |
| 2025/0255727 A1 | 8/2025 | Slocum, Jr. et al. | |

FOREIGN PATENT DOCUMENTS

| | | | |
|---|---|---|---|
| EP | 0103697 A1 | 3/1984 | |
| EP | 0577529 A1 | 1/1994 | |
| JP | 2013501555 A | 1/2013 | |
| JP | 2017505214 A | 2/2017 | |
| WO | 2011150238 A1 | 12/2011 | |
| WO | 2013009966 A2 | 1/2013 | |
| WO | 2013063314 A1 | 5/2013 | |
| WO | 2015118517 A1 | 8/2015 | |
| WO | 2018085329 A1 | 5/2018 | |

OTHER PUBLICATIONS

Non Final Office Action for U.S. Appl. No. 16/950,304, mailed Apr. 3, 2023, 26 pages.

Non Final Office Action for U.S. Appl. No. 16/950,074, dated Mar. 10, 2023, 27 pages.

Office Action (The Second Office Action) issued Dec. 20, 2024, in corresponding Chinese Patent Application No. 202110988219.7 and an English translation of the Office Action. (16 pages).

Office Action (The Second Office Action) issued Nov. 2, 2024, by the State Intellectual Property Office of People's Republic of China in corresponding Chinese Patent Application No. 201910783633.7 and an English translation. (14 pages).

Office Action (Notice of Reasons for Rejection) issued Jan. 21, 2025, by the Japanese Patent Office in corresponding Japanese Patent Application No. 2023-187739 and an English translation of the Office Action. (6 pages).

The Extended European Search Report issued Jul. 10, 2025, by the European Patent Office in corresponding European Patent Application No. 25157720.1-1122. (7 pages).

Office Action (Examination report No. 1 for standard patent application) issued Aug. 20, 2024, by the Australian Government, IP Australia in corresponding Australian Patent Application No. 2019232875. (5 pages).

Office Action (Notice of Reasons for Rejection) issued Aug. 6, 2024, by the Japanese Patent Office in corresponding Japanese Patent Application No. 2023-187739 and an English translation of the Office Action. (9 pages).

Japanese Notice of Reasons for Rejection for Japanese Application No. 2019-206156, mailed Aug. 29, 2023 with translation, 8 pages.

Extended European Search Report for European Application No. 19214530.8, dated Nov. 19, 2020, 12 pages. 2020.

Extended European Search Report for European Application No. 21200744.7, dated Jan. 4, 2022, 8 pages.

Extended European Search Report for European Application No. 21200764.5, dated Dec. 23, 2021, 7 pages.

Extended European Search Report for European Application No. 21208113.7, dated Apr. 20, 2022, 9 pages.

Partial European Search Report for European Application No. 19214530.8, dated Jul. 21, 2020, 12 pages. 2020.

Entire patent prosecution history of U.S. Appl. No. 16/292,467, filed Mar. 5, 2019, entitled, "Cruciate Replacing Artificial Knee." 2020.

Entire patent prosecution history of U.S. Appl. No. 17/167,194, filed Feb. 4, 2021, entitled, "Modular Artificial Knee System."

Office Action (Communication pursuant to Article 94(3) (EPC) issued Jul. 16, 2024, by the European Patent Office in corresponding European Patent Application No. 21 208 113.7-1122. (7 pages).

Office Action (The First Office Action) issued Jun. 28, 2024, in corresponding Chinese Patent Application No. 202110988219.7 and an English translation of the Summary of the Office Action. (10 pages).

Non Final Office Action for U.S. Appl. No. 17/082,568, mailed Apr. 20, 2023, 30 pages.

D'Alessio et al., "On the Application of RRSS Motion Generation and RRSS Axode Generation for the Design of a Concept Prosthetic Knee", Aug. 3, 2016, Mechanics Based Design of Structures and Machines: An International Journal, Taylor and Francis, pp. 1-10 (Year: 2016).

Office Action (Notice of Reasons for Rejection) issued Dec. 16, 2025, by the Japanese Patent Office in corresponding Japanese Patent Application No. 2024-174348 and an English translation of the Office Action. (11 pages).

* cited by examiner

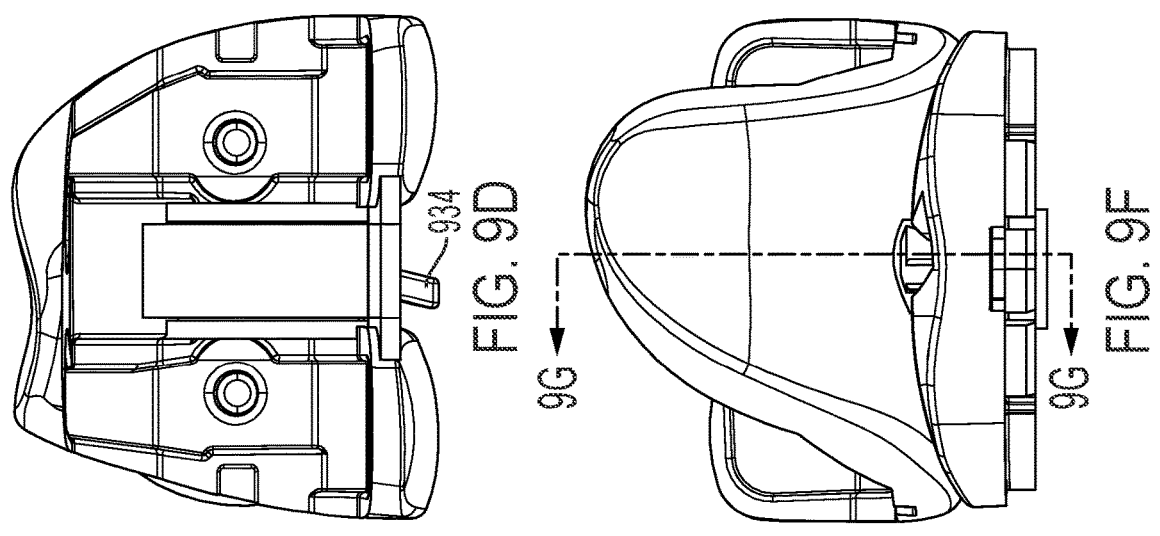
934
FIG. 9D
FIG. 9F
9G
9G
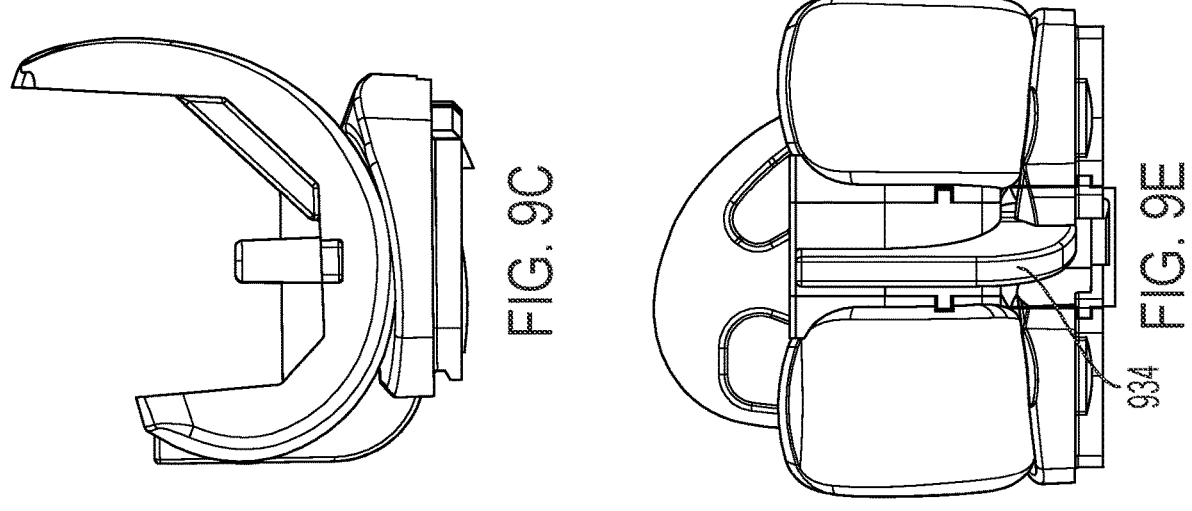
FIG. 9C
FIG. 9E
934

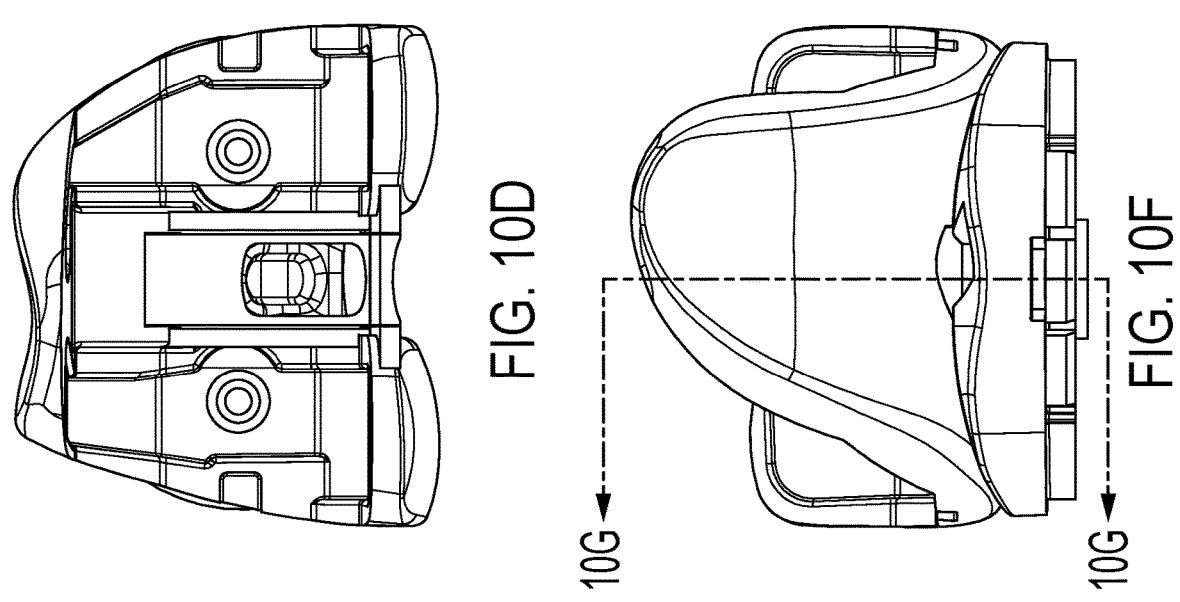
FIG. 10D
FIG. 10F
10G
10G
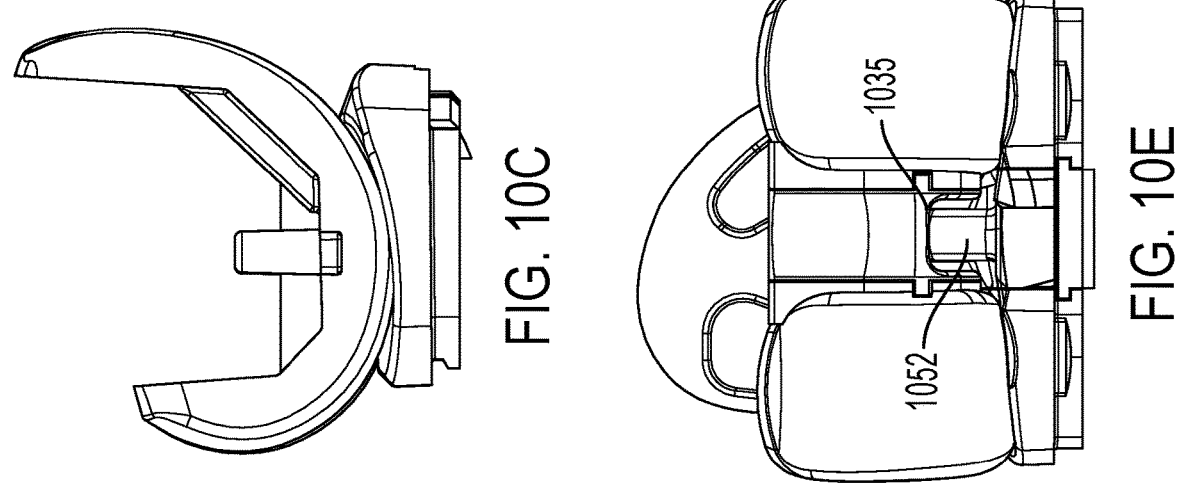
FIG. 10C
FIG. 10E
1035
1052

MODULAR ARTIFICIAL KNEE SYSTEM

CROSS REFERENCE TO RELATED APPLICATION

This application is a continuation of U.S. patent application Ser. No. 17/167,194, filed Feb. 4, 2021, the content of such application being incorporated herein by reference.

FIELD OF THE INVENTION

This invention relates generally to artificial knee prostheses used for Total Knee Replacement (TKR), and more particularly, to a knee joint prosthesis having an artificial anterior cruciate ligament (ACL) and/or posterior cruciate ligament (PCL).

BACKGROUND OF THE INVENTION

As is described in U.S. Patent App. Pub. No. 2017/0252173 to Garino, which is incorporated by reference herein in its entirety and for all purposes, prosthetic knees generally include three main components, a femoral component (FIGS. 1A and 1B), which is attached to the distal end of the femur, a tibial baseplate (FIGS. 2A and 2B), which is implanted onto the proximal end of the tibia, and an articular tibial insert (FIGS. 3A and 3B), which is mounted onto the tibial baseplate and provides a frictional surface for the femoral component. The components are designed to simulate a joint and the associated mechanics of a human knee throughout the knee's range of motion. The components are generally provided in a variety of shapes with varying dimensions (identified as dimensions A-H and J-T in FIGS. 1A to 3B), so that a physician is able to select the optimal combination of components depending on the specific anatomy of the patient. The size and shape of the knee is dependent on various factors including age, gender, and size of the patient. Therefore, a fairly large inventory of components are generally made available, so that the prosthetic knee may be tailored for the patient.

During the course of a routine knee construction with a TKR, the ACL is removed in a vast majority of all cases and depending on the selected TKR design, the patient's PCL is either retained or substituted with some mechanism to replace the lost function of the PCL. Even when the PCL is retained, often a portion of the PCL must be cut or partially cut during surgery to aid in the balancing of the knee replacement. When the PCL is completely removed, the PCL is substituted by a post and cam mechanism.

A TKR generally comprises a femoral component 10, a tibial baseplate 16 having a post 18 that is implanted within a bore formed in the tibia, and an articular insert 22 that resides on a top mounting portion 20 of the tibial baseplate 16 for interfacing with the femoral component 10. Articular insert 22 may be either separate from tibial baseplate 16, as shown, or integrated with tibial baseplate 16 into a single component. The articular insert 22 and tibial baseplate 16 may be referred to herein either together or individually as a "tibial component."

Referring to FIGS. 1A, 1B, 3A, and 3B, an illustration of a typical design of a post and cam mechanism is provided. An articular insert 22 includes an extension 24 that protrudes into an opening 12 of the femoral component 10. A box 11 having upwardly projecting walls is formed on the interior side of the femoral component 10 and includes an interior region that intersects the opening 12. The extension 24 includes a posterior surface 25 that is intended to be in frictional contact with the posterior surface 14 of the opening 12 when the joint is flexed. The resistance generated when the extension 24 bears against the posterior surface 14 of the opening 12 in the femoral component 10 is intended to simulate the resistance that would have been generated by a healthy posterior cruciate ligament (PCL).

Cam and post mechanisms have been manufactured that partially replace the function of an ACL by creating a cam surface between the anterior surface of the extension 24 and the anterior surface of the opening 12; however, this solution provides only a partial substitution of an ACL because the anterior side of the extension 24 is at best able to contact the anterior side of the opening only between 0 to 20 degrees of flexion.

The lack of an anatomically correct replacement may result in a TKR having reduced functionality as compared to the original knee. This may create difficulties during physical therapy following surgery, as well as limit the patient's ability or desire to participate in physical activity following therapy. Virtually all modern total knee replacements sacrifice the ACL or inadequately substitute it with a crude cam and post mechanism, thus leaving the reconstructed knee with kinematics similar to that of an ACL-deficient knee. Normal knee kinematics therefore remain elusive. In addition, the lack of proper interplay between an ACL and PCL (which together drive normal knee kinematics) leaves the TKR reconstruction short of producing a relatively normal knee for the patient.

Given the complexity of the mechanics of a knee joint and the difficulty for patients to adjust to an artificial knee after surgery, an anatomically correct knee replacement system is needed that more accurately simulates the resilience and support formerly provided by the removed ligaments. In order to provide a more anatomically correct TKR, prosthesis embodiments that replicate the function provided by both the ACL and PCL are desirable.

Referring now to FIG. 4, a healthy human knee is illustrated with a loop 30, representing an exemplary artificial ACL/PCL ligament, drawn over the location of the original anatomical ACL and PCL. The section of the loop 30 constituting the artificial PCL is bounded by points 26A and 26B. The section of the loop 30 constituting the artificial ACL is bounded by points 28A and 28B.

Referring now to FIGS. 5, 6A, and 6B illustrating an embodiment disclosed in U.S. Patent App. Pub. No. 2017/0252173 to Garino, the connection points 26a, 26b, 28a, and 28b of the artificial material, provided as ligament 44, and the lengths spanning between the connection points, provided as an outline of the artificial ligament 44, are configured to simulate the dimensions and attachment points of the ACL and PCL in a human knee, as illustrated in FIG. 4. At least one length of artificial ligament may be provided to connect the articular insert 22 and femoral component 10 of a TKR.

While U.S. Patent App. Pub. No. 2017/0252173 to Garino provides solutions to these complexities, developments in this area are continually sought in the interest of improving the mechanics of a knee joint.

SUMMARY OF THE INVENTION

In one embodiment of the present invention, a modular knee joint prosthesis is configured to move between an extended position and a flexion position. The modular knee joint prosthesis includes a femoral component that is configured to be mounted to a femur. The femoral component has a first cutout or opening in a central region thereof for receiving a femoral insert. The modular knee joint prosthesis also includes a tibial component that is configured to (i) be mounted either directly or indirectly to a tibia, and (ii) engage the femoral component. The tibial component has a second cutout or opening in a central region thereof for receiving a tibial insert.

In another embodiment of the present invention, a kit includes the above-described modular knee joint prosthesis, at least two of the femoral inserts having different geometries, and at least two of the tibial inserts having different geometries. Different inserts may be selected based upon various factors including age, gender, and size of the patient.

BRIEF DESCRIPTION OF THE FIGURES

FIGS. 9C-9F depict side elevation, top plan, rear elevation and front elevation views, respectively, of the modular knee joint prosthesis of FIG. 9A.

FIGS. 10C-10F depict side elevation, top plan, rear elevation and front elevation views, respectively, of the modular knee joint prosthesis of FIG. 10A.

DETAILED DESCRIPTION

Figure 1A:
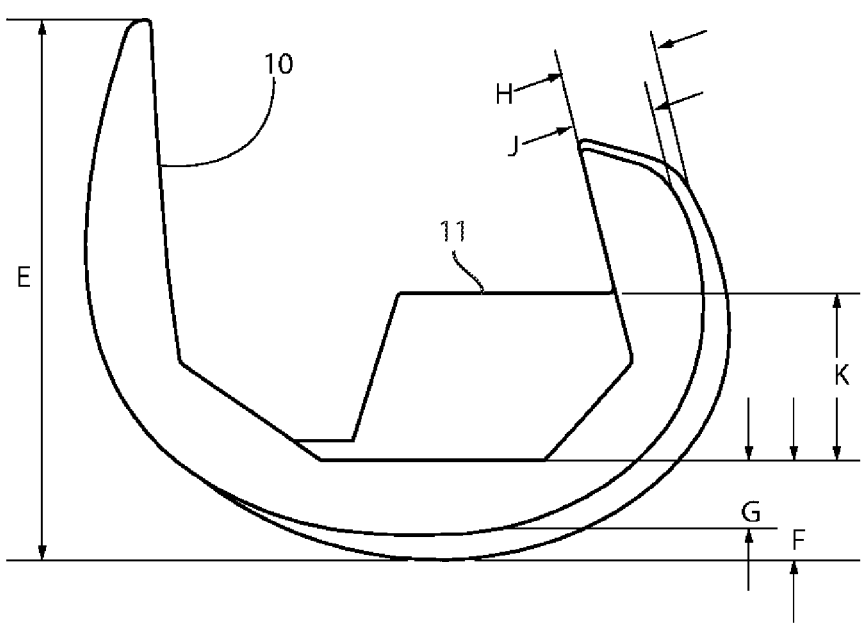
FIG. 1A is a side view of a femoral component for a knee joint prosthesis known by those of ordinary skill in the art.
Figure 1B:
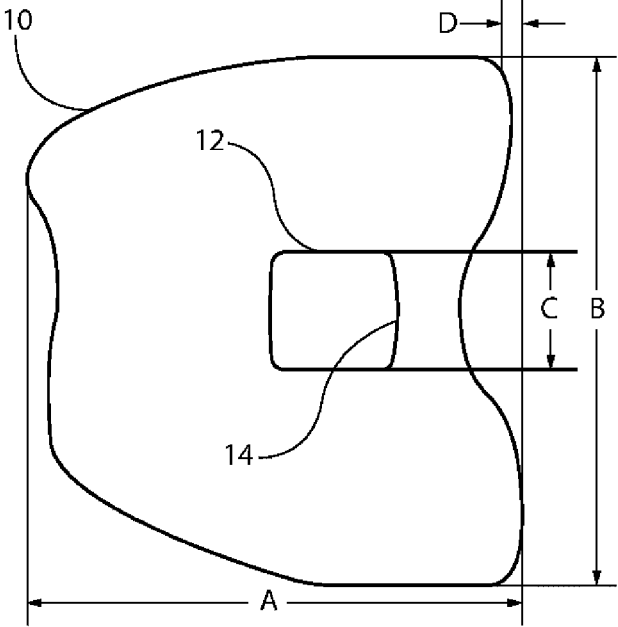
FIG. 1B is a bottom view of the femoral component of FIG. 1A.

The present invention provides various embodiments of a knee joint prosthesis. In the figures, 'A' represents the anterior side or direction, 'P' represents the posterior side or direction, 'M' represents the medial side or direction, and 'L' represents the lateral side or direction.

FIGS. 7A-7H depict a modular knee joint prosthesis 700 according to a first exemplary embodiment. Although a prosthesis 700 for a left knee is shown and described hereinafter it should be understood that the right knee prosthesis is substantially similar and the explanation that follows also applies to the right knee prosthesis.

Prosthesis 700 generally comprises a modular femoral component 702, a femoral insert 705 that is configured to be mounted to the femoral component 702, a modular articular component 704, and a tibial insert 706 that is configured to be mounted to the articular component 704.

Modular femoral component 702 includes a U-shaped body having opposing condyles 710. Pins 711 extend upwardly from the inside surface of component 702 for implantation of femoral component 702 into a femur bone, as is known in the art. A rectangular cutout 712 is defined in the femoral component 702 at a central location between the condyles 710. Cutout 712 extends in the posterior-anterior direction and in the sagittal plane. Cutout 712 includes an opening at the posterior side of component 702. Cutout 712 extends through the entire wall thickness of component 702. Cutout 712 includes three interconnected and interior facing sides, namely, a lateral side extending in the sagittal plane, a medial side extending in the sagittal plane, and an anterior side that connects the lateral and medial sides. The posterior side of cutout 712 is open for receiving the insert 705.

A relief is formed on each of the opposing medial and lateral sides of cutout 712. Together the reliefs form a slot or track 713 that is configured to receive rails 715 (i.e., shoulders) formed on opposing sides of femoral insert 705 such that insert 705 can be installed on component 702. It should be understood that track 713 may be disposed on insert 705 and rails 715 may be disposed on component 702 to achieve either the same or a similar result.

It should be understood that means for mounting insert 705 to component 702, other than the tracks 713 and rails 715, may be provided. The means for mounting may alternatively comprise a slot, guide, rail, snap feature, friction fit, interference fit, fastener (screw, bolt, nut), weld, adhesive, dovetail (or other mating surface).

Figure 2A:
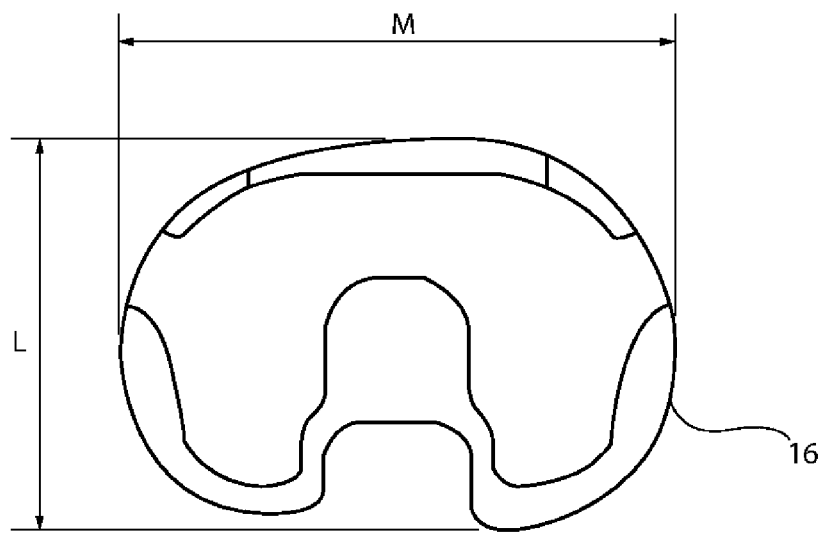
FIG. 2A is a top view of a tibial component for a knee joint prosthesis known by those of ordinary skill in the art.
Figure 2B:
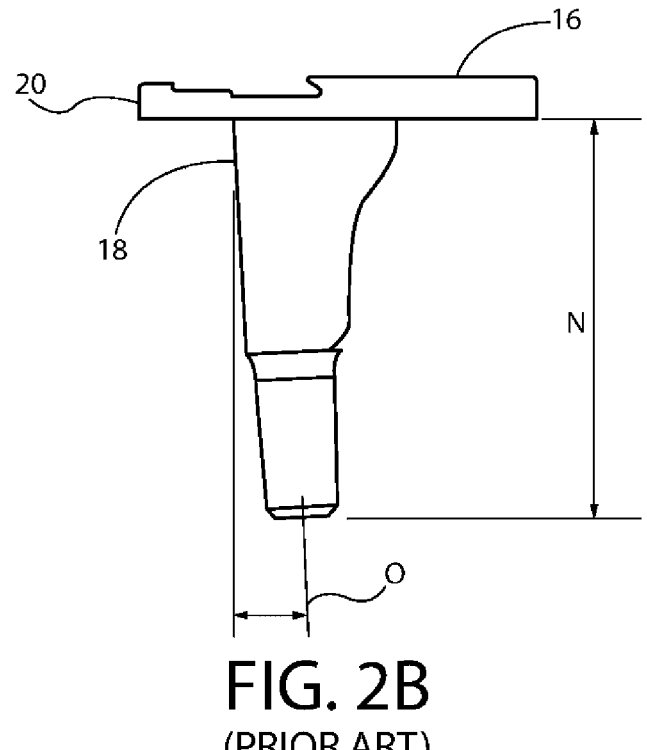
FIG. 2B is a side view of the tibial component of FIG. 2A.
Figure 3A:
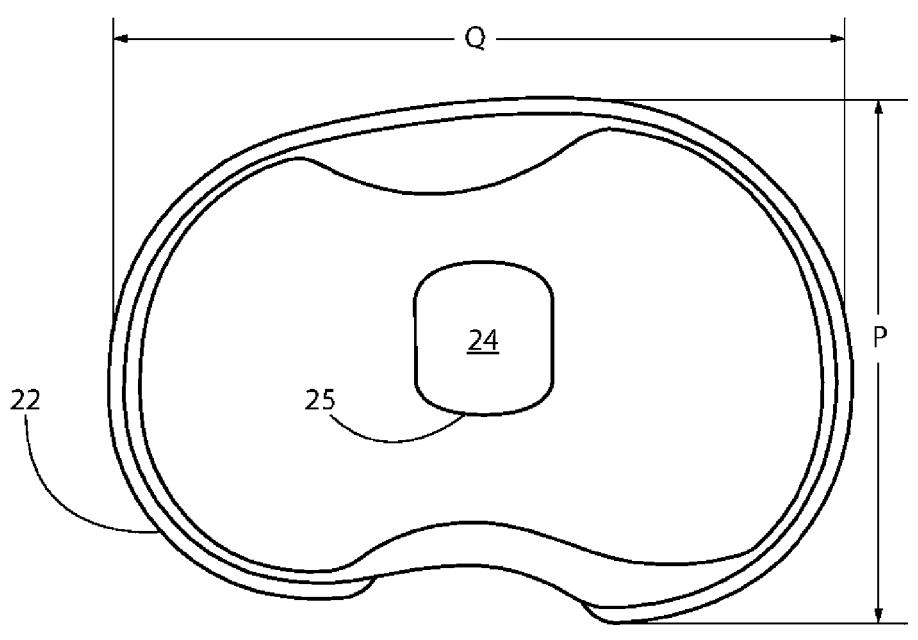
FIG. 3A is a top view of an articular insert for a knee joint prosthesis known by those of ordinary skill in the art.
Figure 3B:
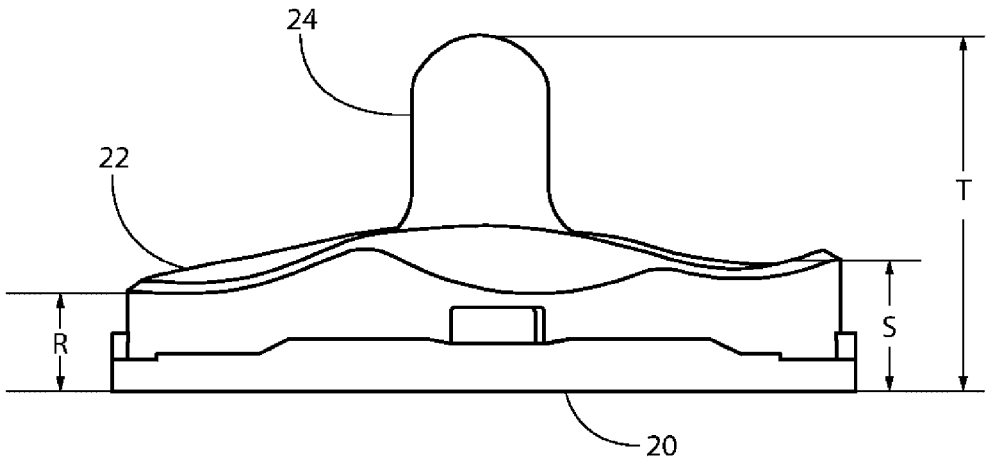
FIG. 3B is a front view of the articular insert of FIG. 3B mounted on the baseplate of a tibial component.
Figure 4:
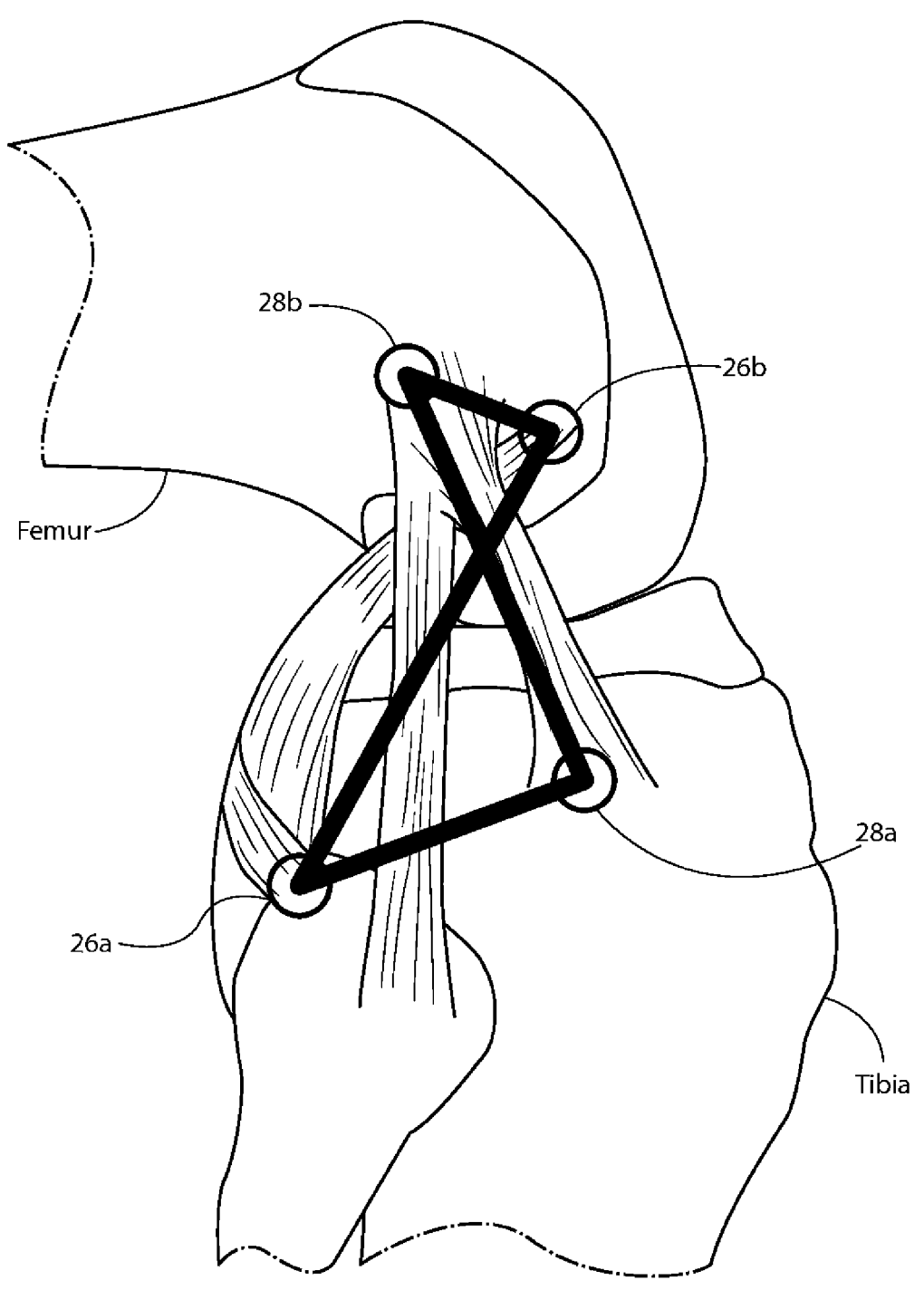
FIG. 4 is a side view of a knee joint illustrating the anatomical location of the ACL and PCL and the configuration of an artificial material intended to replace the ACL and PCL.
Figure 5:
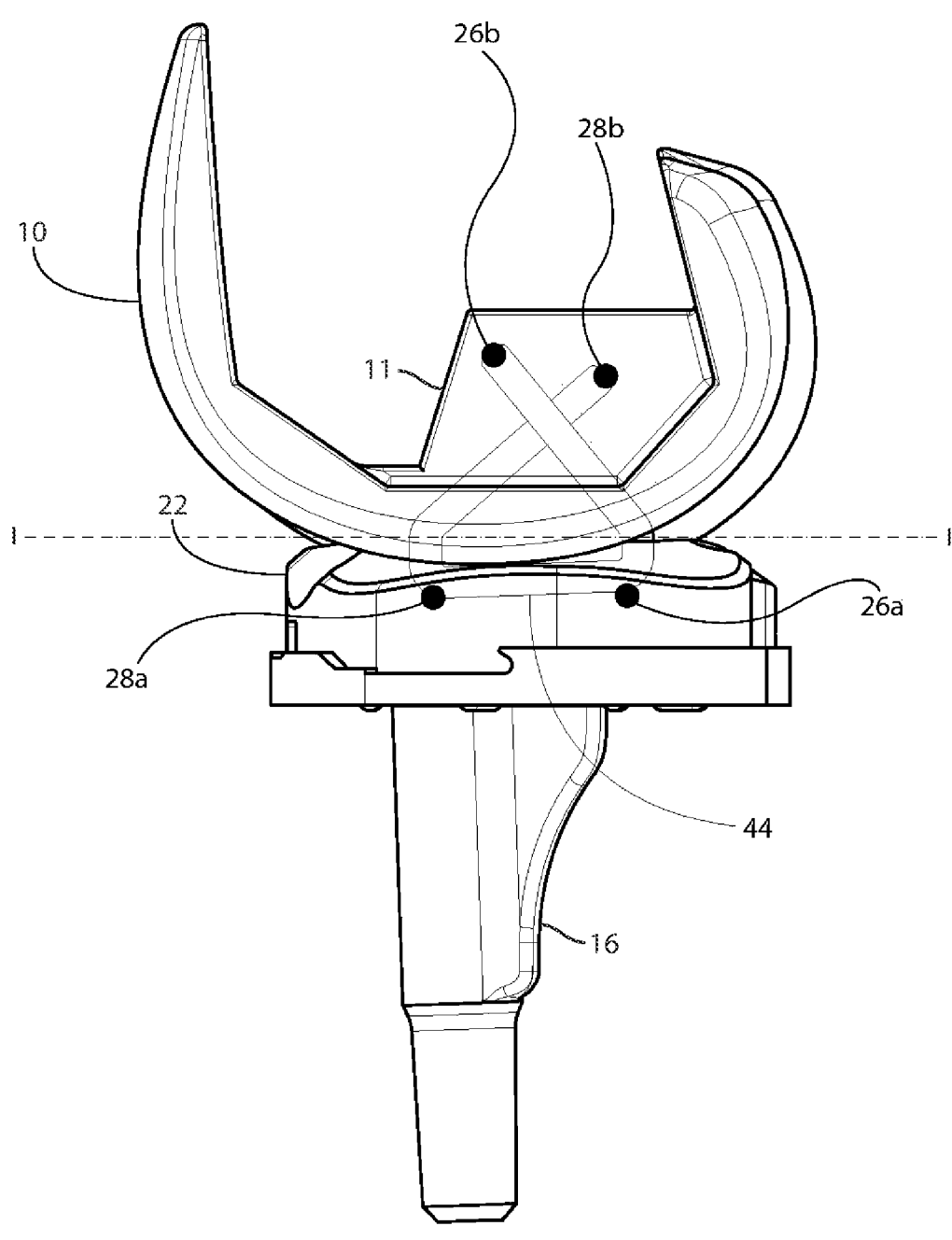
FIG. 5 is a side view of a femoral component, articular insert, and artificial ligament for a TKR according to the prior art.
Figures 6A, 6B:
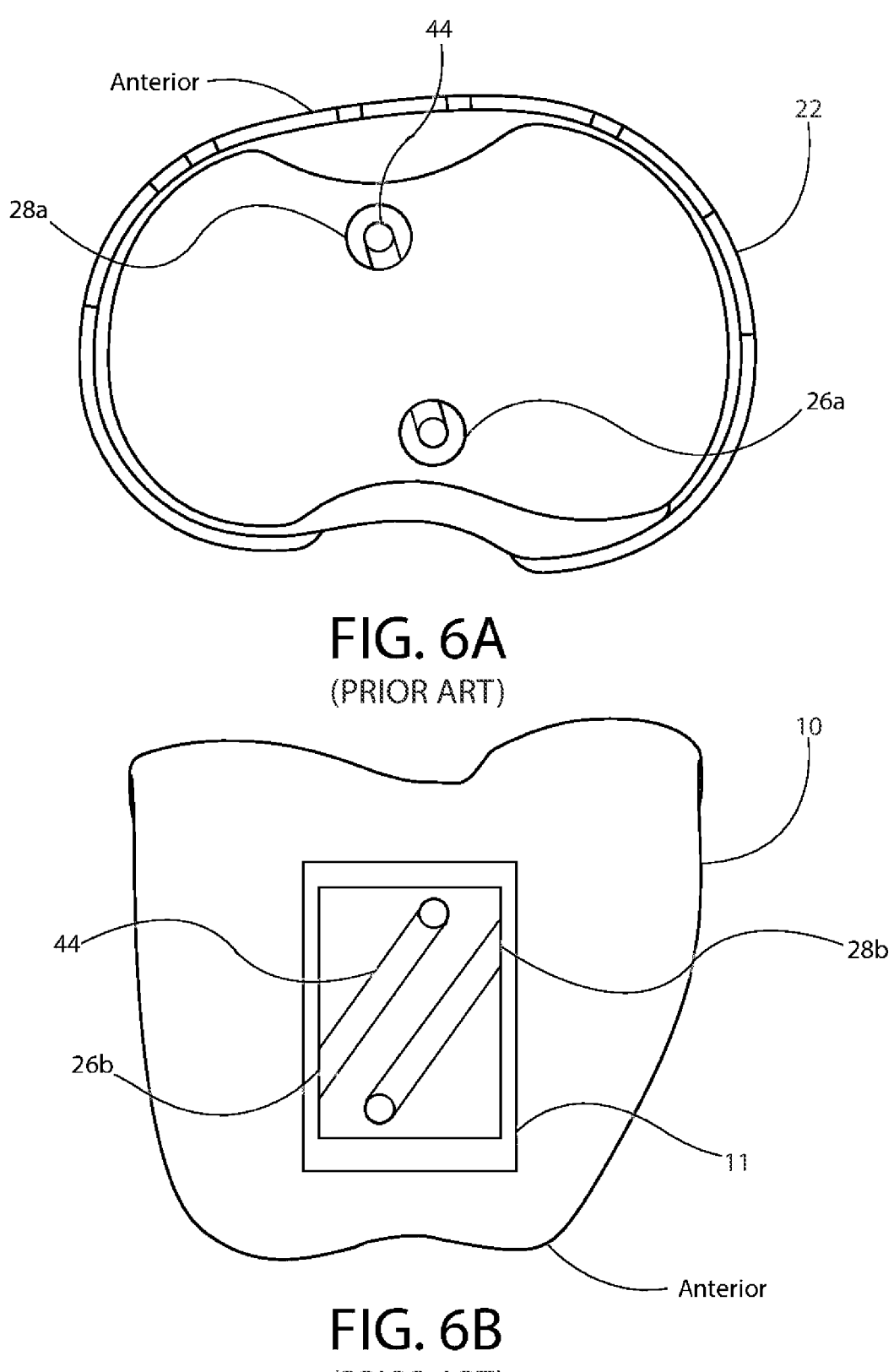
FIG. 6A is a top view of a cross-section along line I-I of FIG. 5.
FIG. 6B is a bottom view of a cross-section along line I-I of FIG. 5.

Modular articular component 704 is configured to reside on a top mounting portion of a tibial component (not shown) for interfacing with femoral component 702. Articular component 704 is configured to be mounted to the tibial baseplate 16 (see FIGS. 2B and 5) that is fixedly mounted to the tibia. Alternatively, and although not shown, articular component 704 may be integrated with the tibial baseplate 16 to form a single unitary tibial component that is fixedly mounted to the tibia. Thus, a "tibial component" may comprise either articular component 704 (alone) or both articular component 704 and tibial baseplate 16.

Articular component 704 includes two concave surfaces 721 for physically engaging with the convexly shaped condyles 710 of femoral component 702 as prosthesis 700 is moved between the flexion and extension positions. A rectangular cutout 723 is defined in the articular component 704 at a central location between the concave surfaces 721. Cutout 723 extends in the posterior-anterior direction and in the sagittal plane. Cutout 723 includes an opening at the posterior side of articular component 704. Cutout 723 extends through the wall thickness of articular component 704. Cutout 723 includes three interconnected and interior facing sides, namely, a lateral side extending in the sagittal plane, a medial side extending in the sagittal plane, and an anterior side that connects the lateral and medial sides. A relief is formed on each of the opposing medial and lateral sides of cutout 723. Together the reliefs form a slot or track 724 that is configured to receive rails 725 (shoulders) formed on opposing sides of tibial insert 706 such that insert 706 can be installed on articular component 704 by sliding rails 725 along tracks 724. It should be understood that track 724 may be disposed on insert 706 while rails 725 may be disposed on articular component 704 to achieve either the same or a similar result.

It should be understood that means for mounting insert 706 to articular component 704, other than the tracks 724 and rails 725, may be provided. The means for mounting may alternatively comprise a slot, guide, rail, snap feature, friction fit, interference fit, fastener (screw, bolt, nut), weld, adhesive, dovetail (or other mating surface).

Femoral component 702 and articular component 704 are modular components that are common amongst the first through fourth embodiments. Femoral component 702 and articular component 704 may together form a modular sub-assembly.

Turning now to the components that are capable of being selectively installed on those modular components 702 and 704, femoral insert 705 is configured to be mounted to femoral component 702, and tibial insert 706 is configured to be mounted to articular component 704 (otherwise referred to tibial component 704). Femoral and tibial inserts 705 and 706 work together to guide motion of the prosthesis 700 between the flexion and extension positions shown in FIGS. 7G and 7H.

Femoral insert 705 comprises an L-shaped body. The body defines an elongated horizontal portion 731 on which rails 715 protrude from the opposing side surfaces thereof. The horizontal portion 731 is sized to fit snugly within cutout 712 of femoral component 702. A vertical portion 733 of the body extends orthogonally from the horizontal portion 731. In an assembled form, the vertical portion 733 sits flush with and bridges the condyles 710 of femoral component 702. Vertical portion 733 also serves as a finger tab for ease of manual insertion and/or removal of the insert 705 onto/from the femoral component 702. Femoral insert 705 may be either releasably or non-releasably connected to femoral component 702.

A gear 734, in the form of a convex surface, protrudes outwardly from the front and rear exterior facing surfaces of the L-shaped body of insert 705. Gear 734 comprises a plurality of individual gear teeth having rounded outer surfaces. The gear teeth are uniformly spaced apart along the outer perimeter of gear 734. Gear 734 follows a helical path, as can be viewed in FIGS. 7D and 7E. Specifically, gear 734 curves about (i) its own axis 740 (FIGS. 7G and 7H) extending in the medial-lateral direction and (ii) an axis that extends in the anterior-posterior direction (see FIG. 7E). Stated differently, gear 734 curves along two different axes that are oriented orthogonal to each other. Gear 734 resides on the front and rear surfaces of the L-shaped body, whereas the rails 715 are disposed on the left and right sides of the body, and the top and rear facing surfaces are planar. Femoral insert 705 may be a unitary, monolithic component.

Tibial insert 706 comprises an elongated rectangular body. Rails 725 extend in the anterior-posterior direction and protrude from the opposing side surfaces of the body. Rails 725 are sized to fit within the track 724 formed on articular component 704, as described above, such that rails 725 slide in their corresponding tracks 724. A finger tab 744 is defined on the lower posterior edge of insert 706 to ease manual handling of insert 706. Tibial insert 706 may be either releasably or non-releasably connected to articular component 704.

Figures 7A, 7B:
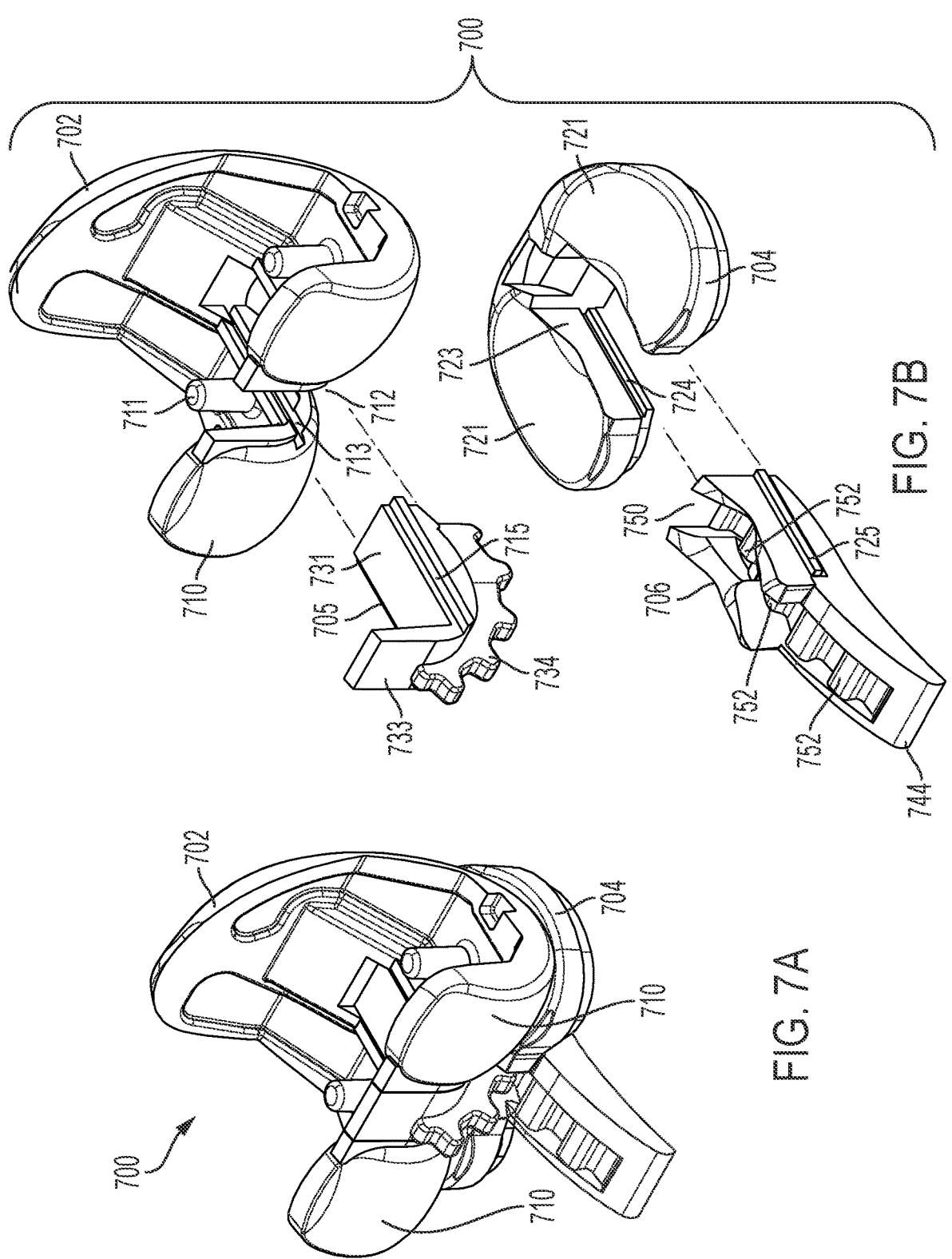
FIG. 7A is an assembled view of a modular knee joint prosthesis as viewed from the top, left and posterior sides, and according to a first exemplary embodiment.
FIG. 7B is an exploded view of the modular knee joint prosthesis of FIG. 7A.
Figures 7C, 7D, 7E, 7F:
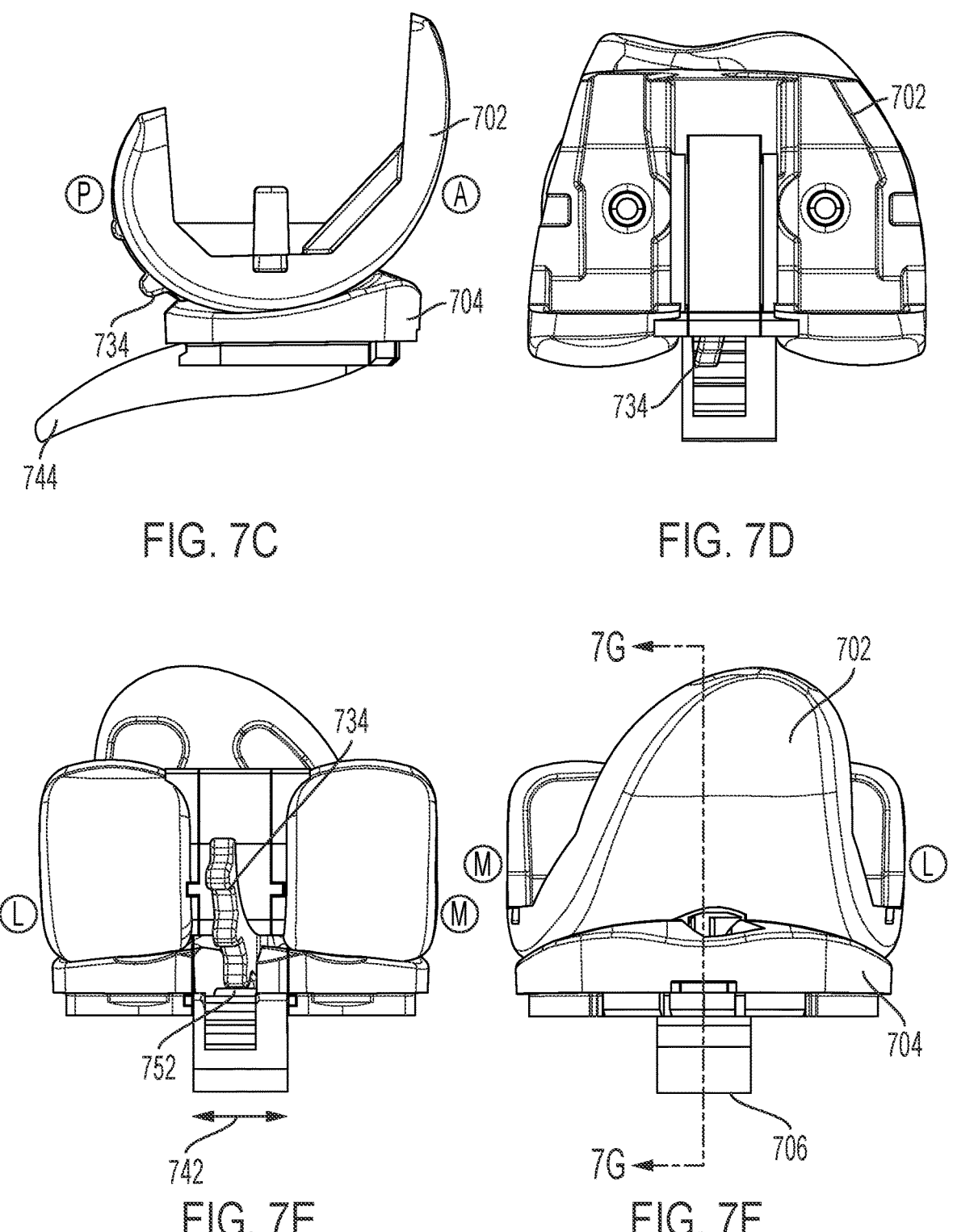
FIGS. 7C-7F depict side elevation, top plan, rear/posterior elevation and front/anterior elevation views, respectively, of the modular knee joint prosthesis of FIG. 7A.
Figure 7H:
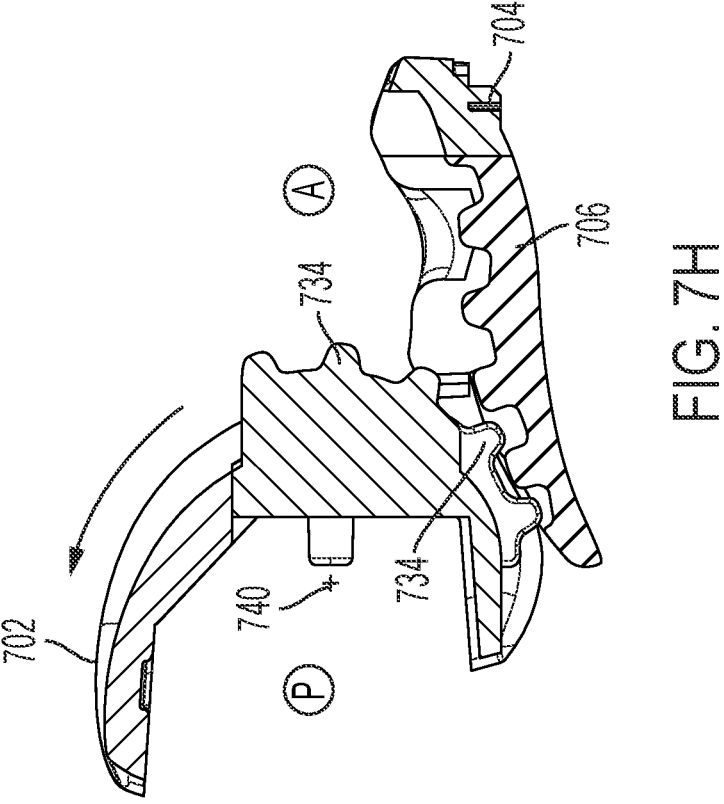
FIG. 7H depicts another cross-sectional view of the modular knee joint prosthesis like FIG. 7G, but with the modular knee joint prosthesis shown in a flexion position.

A curved channel 750 extends in the anterior-posterior direction through the body of the insert 706. The channel 750 has opposing curved sidewalls that face each other. The channel 750 curves about a vertical axis (in the superior-inferior direction or along the sagittal plane), as shown in FIG. 7B, for example. The base surface of the channel 750 has a series of gear teeth 752 extending upwards therefrom for meshing with the teeth of gear 734. The base surface may be flat (with the exception of the teeth 752), or the base surface may be curved about axis 740 (FIG. 7H). Insert 706 may be a unitary, monolithic component.

Figure 7G:
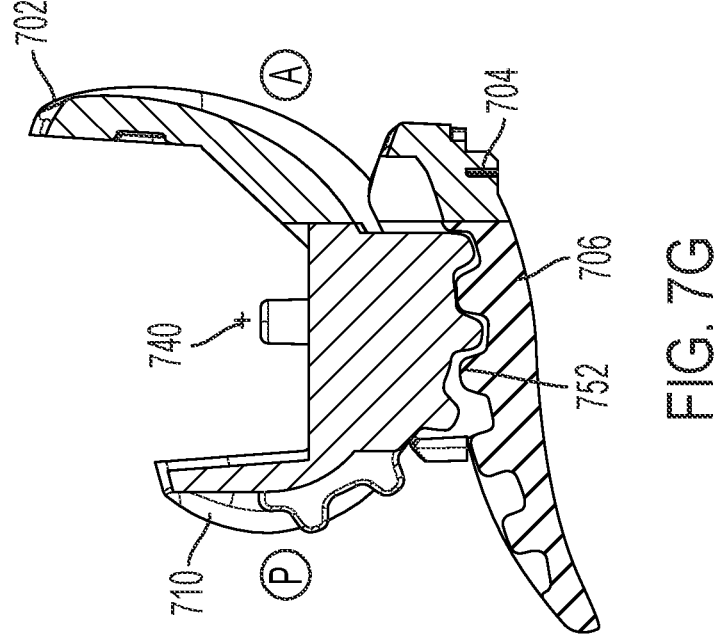
FIG. 7G depicts a cross-sectional view of the modular knee joint prosthesis of FIG. 7F taken along the lines 7G-7G, wherein the modular knee joint prosthesis is shown in an extended position.
Figures 8A, 8B:
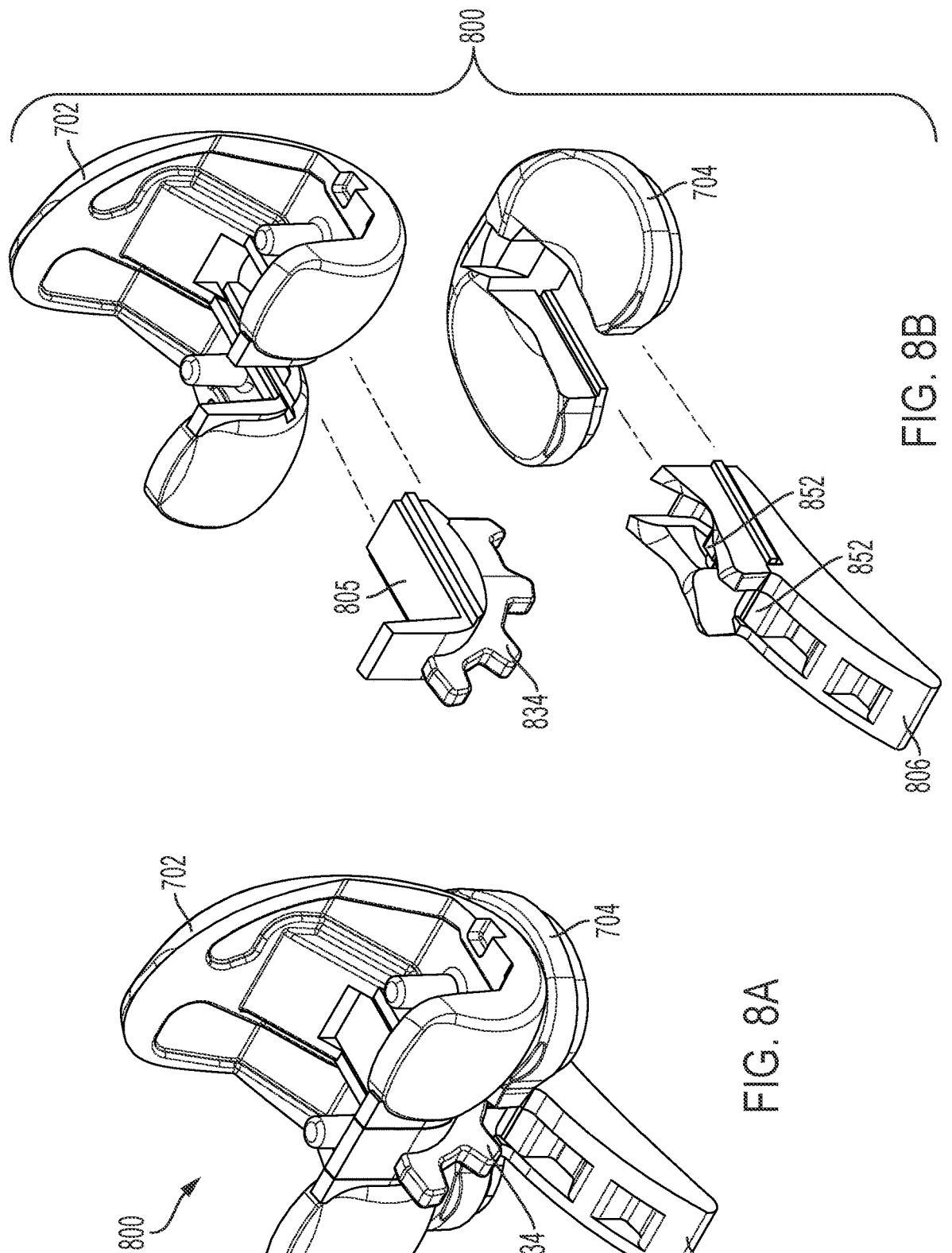
FIG. 8A is an assembled view of a modular knee joint prosthesis according to a second exemplary embodiment.
FIG. 8B is an exploded view of the modular knee joint prosthesis of FIG. 8A.
Figure 8C:
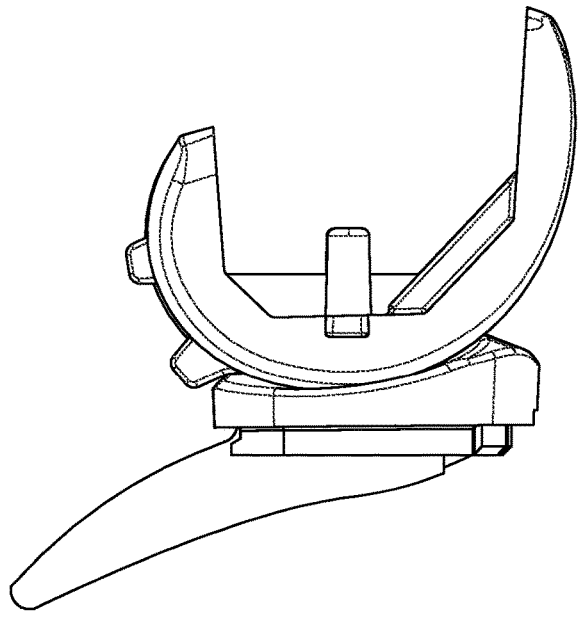
FIGS. 8C-8F depict side elevation, top plan, rear elevation and front elevation views, respectively, of the modular knee joint prosthesis of FIG. 8A.
Figure 8D:
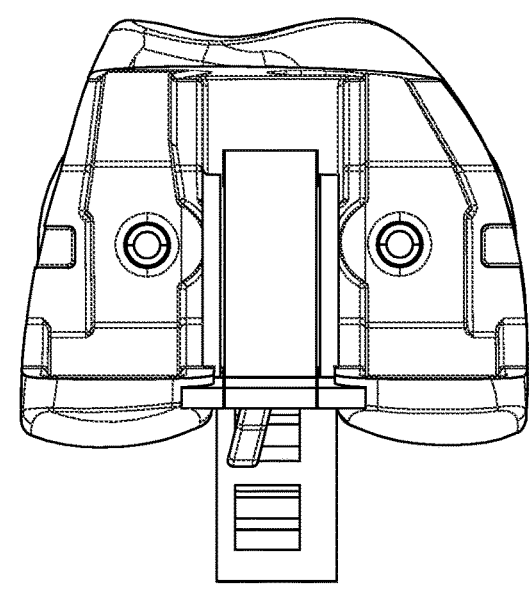
Figure 8E:
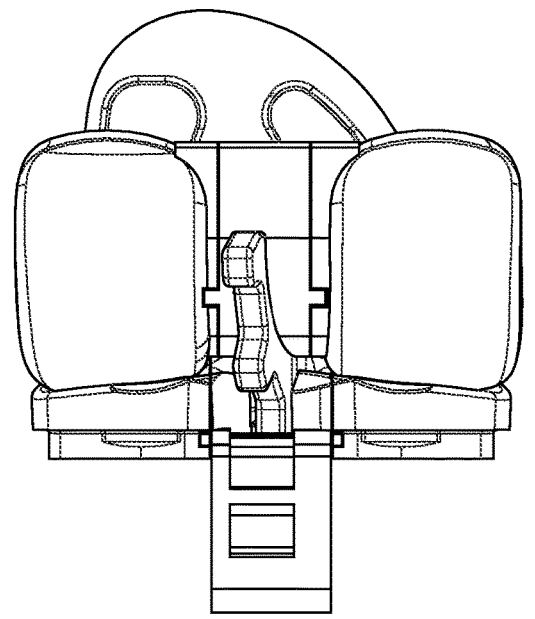
Figure 8F:
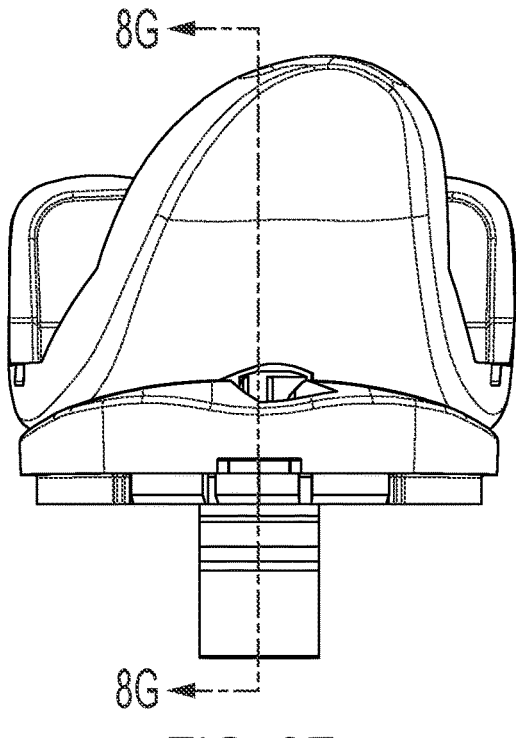
Figure 8H:
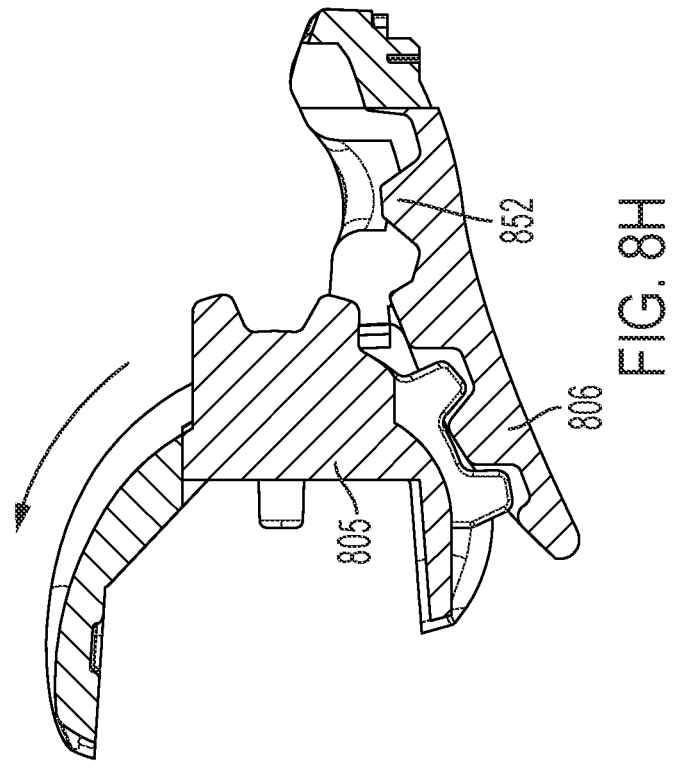
FIG. 8H depicts another cross-sectional view of the modular knee joint prosthesis like FIG. 8G, but with the modular knee joint prosthesis shown in a flexion position.
Figure 8G:
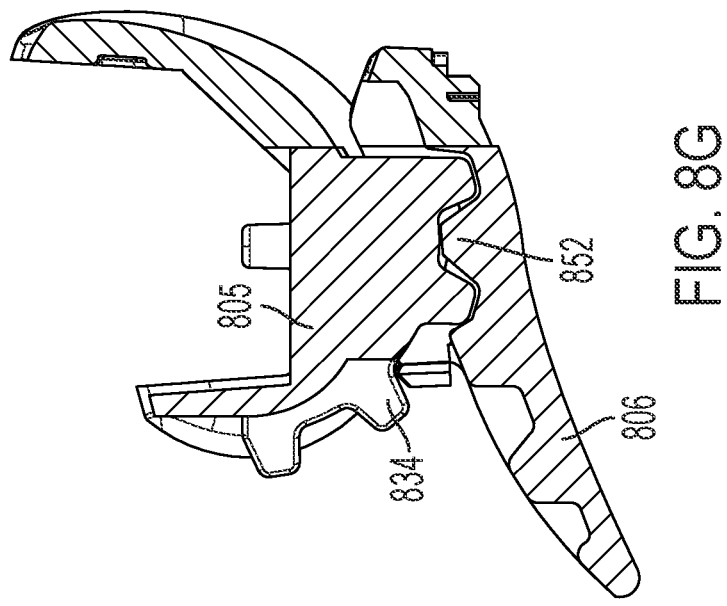
FIG. 8G depicts a cross-sectional view of the modular knee joint prosthesis of FIG. 8F taken along the lines 8G-8G, wherein the modular knee joint prosthesis is shown in an extended position.
Figures 9A, 9B:
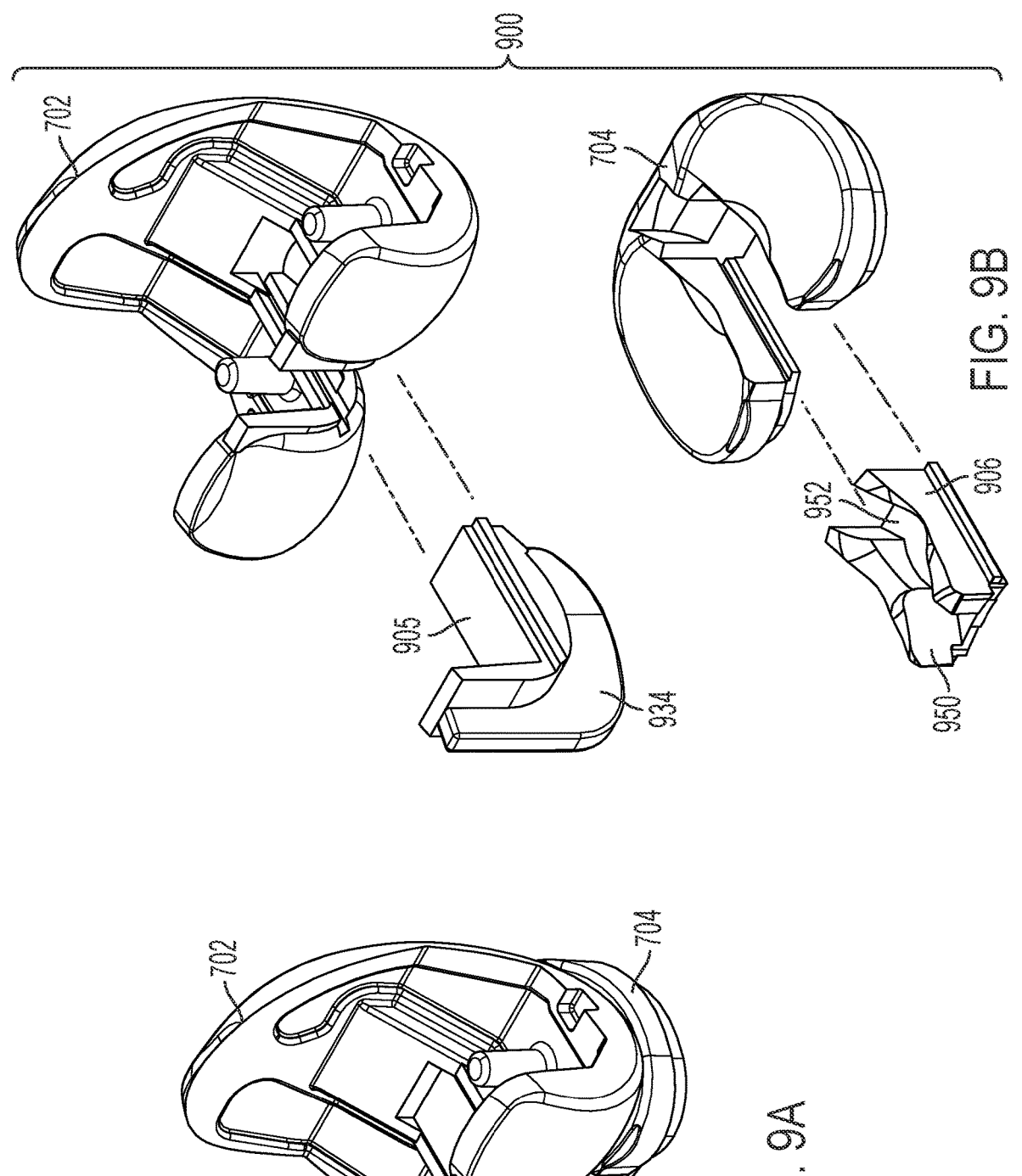
FIG. 9A is an assembled view of a modular knee joint prosthesis according to a third exemplary embodiment.
FIG. 9B is an exploded view of the modular knee joint prosthesis of FIG. 9A.
Figure 9H:
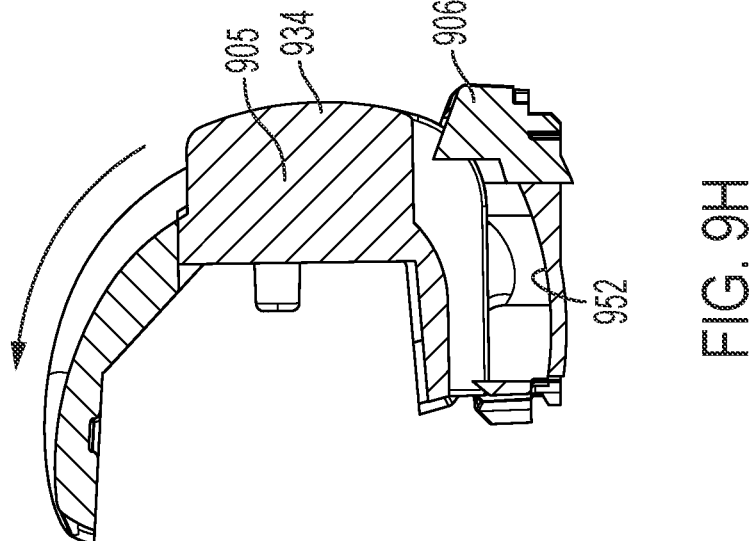
FIG. 9H depicts another cross-sectional view of the modular knee joint prosthesis like FIG. 9G, but with the modular knee joint prosthesis shown in a flexion position.
Figure 9G:
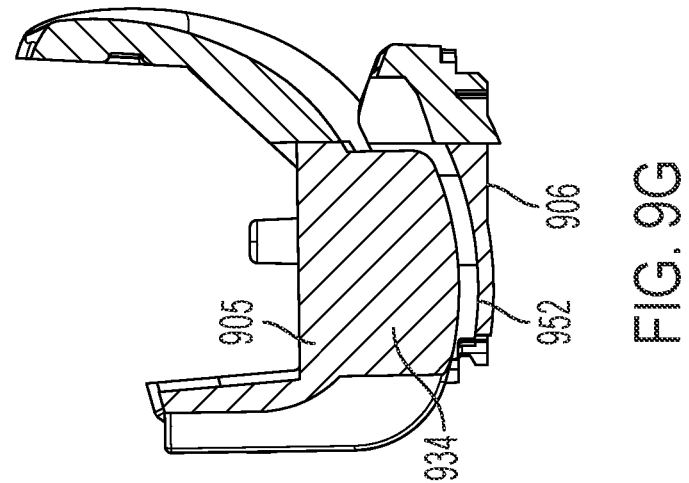
FIG. 9G depicts a cross-sectional view of the modular knee joint prosthesis of FIG. 9F taken along the lines 9G-9G, wherein the modular knee joint prosthesis is shown in an extended position.
Figures 10A, 10B:
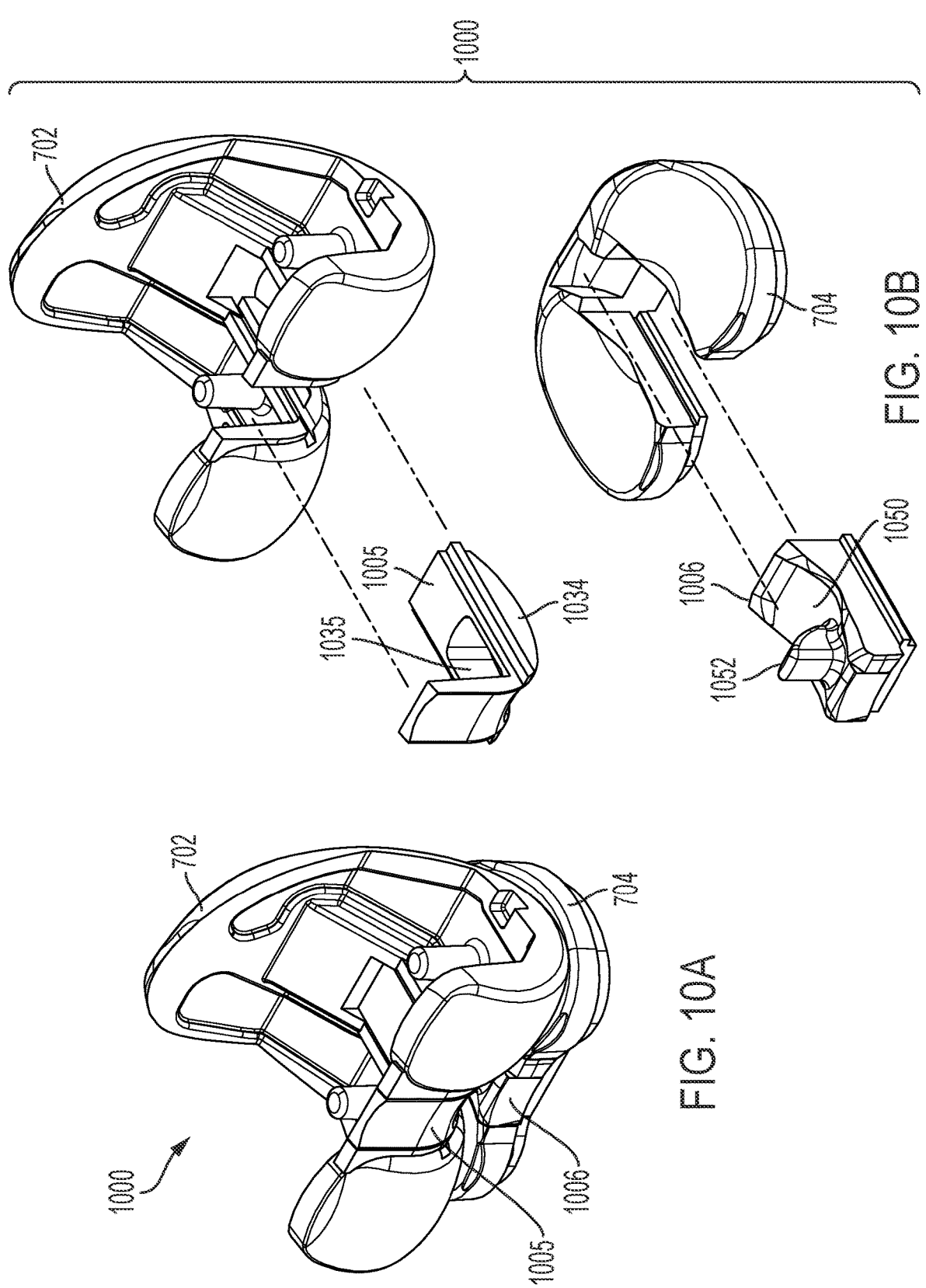
FIG. 10A is an assembled view of a modular knee joint prosthesis according to a fourth exemplary embodiment.
FIG. 10B is an exploded view of the modular knee joint prosthesis of FIG. 10A.
Figure 10H:
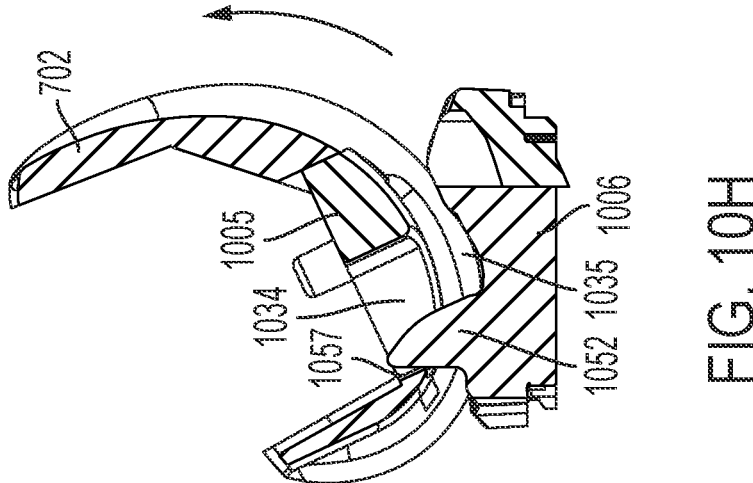
FIG. 10H depicts another cross-sectional view of the modular knee joint prosthesis like FIG. 10G, but with the modular knee joint prosthesis shown in a flexion position.
Figure 10G:
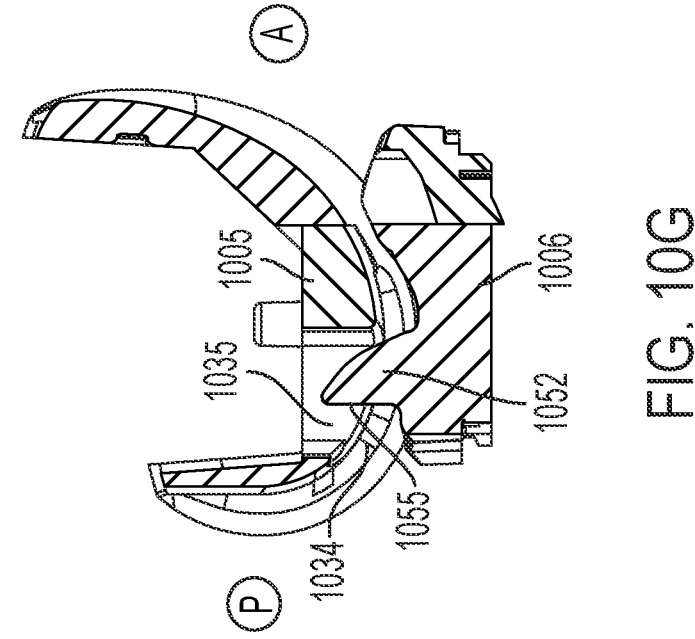
FIG. 10G depicts a cross-sectional view of the modular knee joint prosthesis of FIG. 10F taken along the lines 10G-10G, wherein the modular knee joint prosthesis is shown in an extended position.

Turning now to FIGS. 7G and 7H, the gear teeth 752 on the articular component 704 are meshed with the gear teeth 734 of the femoral component 702, such that the articular component 704 rotates on the femoral component 702, or vice versa. As the femoral component 702 rotates in a posterior direction to the flexion position shown in FIG. 7H (as designated by the arrow), the meshing teeth do not slide past one another. The slight rotation of the articular component 704 in the medial-lateral direction as the prosthesis 700 is moved between the flexion and extension positions, as a result of the curvature of gear teeth 734 in the medial lateral direction, mimics the slight rotation experienced in a real knee joint.

FIGS. 8A-8H depict a modular knee joint prosthesis 800 according to a second exemplary embodiment. It should be understood that prosthesis 800 is similar to prosthesis 700 and only the differences therebetween will be described hereinafter.

Prosthesis 800 includes femoral component 702 and articular component 704, however, it includes different femoral and tibial inserts. As compared with femoral insert

705, femoral insert 805 also has a gear 834, however, gear 834 has a smaller number of individual teeth. Similarly, tibial insert 806 also has a smaller number of individual gear teeth 852. The individual teeth of prosthesis 800 are larger in size than their counterparts in prosthesis 700.

FIGS. 9A-9H depict a modular knee joint prosthesis 900 according to a third exemplary embodiment. It should be understood that prosthesis 900 is also similar to prosthesis 700 and only the differences therebetween will be described hereinafter. Prosthesis 900 includes femoral component 702 and articular component 704, however, it includes different femoral and tibial inserts. As compared with femoral insert 705, femoral insert 905 does not have any teeth. Rather, femoral insert 905 includes a blade 934. The free and lower edge of the blade 934 may be flat and dull, as shown, and is not necessarily sharp.

Like the gear 734, the blade 934 follows a helical path, i.e., the same helical path of gear 734. The tibial insert 906 has a channel 950, like the channel 750 of the insert 706. However, the base surface of the channel 950 is planar and includes no teeth. In operation, the free end of blade 934 both rotates and translates along the flat base surface of the channel 950 between the flexion and extensions positions.

FIGS. 10A-10H depict a modular knee joint prosthesis 1000 according to a fourth exemplary embodiment. It should be understood that prosthesis 1000 is similar to prosthesis 700 and only the differences therebetween will be described hereinafter.

Prosthesis 1000 includes femoral component 702 and articular component 704, however, it includes different femoral and tibial inserts. Femoral insert 1005 includes a lower convex surface 1034, and a substantially rectangular cutout 1035 disposed in a vertical direction (i.e., in the superior-inferior direction when in the extended position) through the thickness of insert 1005.

Tibial insert 1006 includes an upper concave surface 1050 that is shaped and sized to receive the lower convex surface 1034 of the femoral insert 1005. A post 1052 extends upward from the upper concave surface 1050. The post 1052 has a right-triangle shape as viewed in cross-section (FIG. 10G), whereby the hypotenuse of the post 1052 is defined on an anterior side, and a vertical face 1055 of the post 1052 is defined on a posterior side. In an assembled form of prosthesis 1000, post 1052 is fitted within cutout 1035. Post 1052 remains within cutout 1035 as prosthesis 1000 is moved between the extended and flexion positions. Femoral component 702 can be moved toward the flexion position until the vertical face 1055 of post 1052 engages with a bearing surface 1057 on a posterior side of cutout 1035.

It should be understood that each of the femoral inserts and tibial inserts can be used interchangeably with the femoral component 702 and articular component 704, respectively. The various femoral inserts have varying geometries, and similarly, the various tibial inserts have varying geometries. All of the femoral inserts and tibial inserts can be provided with one femoral component 702 and one articular component 704 as a kit, if so desired. In use, different femoral and tibial inserts may be selected by the surgeon based upon various factors including age, gender, ailments, and size of the patient, for example.

The components of the knee joint prosthesis may be made of the same or similar material. In general, however, all materials are preferably inert, not prone to cause infection, and otherwise safe and approved for use as a surgical implant. Exemplary materials include polyethylene, surgically approved metal alloys, surgically approved ceramic materials, or a combination thereof. Any well-known materials in the field of surgical implants may be used to fabricate any of the various embodiments or portions thereof according to the present invention.

While preferred embodiments of the invention have been shown and described herein, it will be understood that such embodiments are provided by way of example only. Numerous variations, changes, and substitutions may occur to those skilled in the art without departing from the spirit of the invention. Accordingly, it is intended that the appended claims cover all such variations that fall within the spirit and scope of the invention.

I claim:

1. A modular knee joint prosthesis configured to move between an extended position and a flexion position, the modular knee joint prosthesis comprising:

a femoral component configured to be mounted to a femur, the femoral component having (i) condyles and (ii) a first cutout or opening located between the condyles, a femoral insert removably mounted within the first cutout or opening of the femoral component by a first sliding rail and slot engagement, the first sliding rail and slot engagement including either elongated rails or elongated slots disposed on opposing sides of the femoral insert and extending in an anterior-posterior direction when the modular knee joint prosthesis is maintained in the extended position, a tibial component configured to (i) be mounted either directly or indirectly to a tibia, and (ii) engage the femoral component, the tibial component having (i) bearing surfaces for directly engaging the condyles of the femoral component, and (ii) a second cutout or opening located between the bearing surfaces, a tibial insert removably mounted within the second cutout or opening of the tibial component by a second sliding rail and slot engagement, the second sliding rail and slot engagement including either elongated rails or elongated slots disposed on opposing sides of the tibial insert and extending in the anterior-posterior direction when the modular knee joint prosthesis is maintained in the extended position, and a femoral gear disposed on the femoral insert and a tibial gear disposed on the tibial insert, wherein the femoral and tibial gears are configured to be meshed together.

2. The modular knee joint prosthesis of claim 1, wherein the femoral and tibial gears are configured to be meshed together in both the extended and flexion positions.

3. The modular knee joint prosthesis of claim 1, wherein the femoral and tibial gears have gear teeth.

4. The modular knee joint prosthesis of claim 1, wherein the tibial component comprises an articular insert, and the second cutout or opening is formed in the articular insert, and wherein the articular insert is configured to be sandwiched between the femoral component and a tibial baseplate that is mounted directly to the tibia.

5. A kit comprising the modular knee joint prosthesis of claim 1 and further comprising at least two of the femoral inserts having different geometries, and at least two of the tibial inserts having different geometries.

6. A modular knee joint prosthesis configured to move between an extended position and a flexion position, the modular knee joint prosthesis comprising:

a femoral component configured to be mounted to a femur, the femoral component having (i) condyles and (ii) a first cutout or opening located between the condyles, a femoral insert mounted within the first cutout or opening of the femoral component, the femoral insert having a femoral gear, a tibial component configured to (i) be mounted either directly or indirectly to a tibia, and (ii) engage the femoral component, the tibial component having (i) bearing surfaces for directly engaging the condyles of the femoral component, and (ii) a second cutout or opening located between the bearing surfaces, a tibial insert mounted within the second cutout or opening of the tibial component, the tibial insert having a tibial gear, wherein the femoral and tibial gears are configured to be meshed together, wherein at least one of the gears follows a helical trajectory to cause movement of the tibial component in either a medial or lateral direction as the knee joint prosthesis is moved to the extended position.

7. A modular knee joint prosthesis configured to move between an extended position and a flexion position, the modular knee joint prosthesis comprising:

a femoral component configured to be mounted to a femur, the femoral component having (i) condyles and (ii) a first cutout or opening located between the condyles, and a femoral insert mounted within the first cutout or opening of the femoral component, the femoral insert having a blade protruding therefrom, a tibial component configured to (i) be mounted either directly or indirectly to a tibia, and (ii) engage the femoral component, the tibial component having (i) bearing surfaces for directly engaging the condyles of the femoral component, and (ii) a second cutout or opening located between the bearing surfaces, and a tibial insert mounted within the second cutout or opening of the tibial component, the tibial insert having a slot disposed therein, wherein the blade is configured to be positioned within the slot in both the extended and flexion positions, wherein the blade follows a helical trajectory to cause movement of the tibial component in either a medial or lateral direction as the knee joint prosthesis is moved to the extended position.

8. A modular knee joint prosthesis configured to move between an extended position and a flexion position, the modular knee joint prosthesis comprising:

a femoral component configured to be mounted to a femur, the femoral component having (i) condyles and (ii) a first cutout or opening located between the condyles, a femoral insert removably mounted within the first cutout or opening of the femoral component by a first sliding rail and slot engagement, the first sliding rail and slot engagement including either elongated rails or elongated slots disposed on opposing sides of the femoral insert and extending in an anterior-posterior direction when the modular knee joint prosthesis is maintained in the extended position, a tibial component configured to (i) be mounted either directly or indirectly to a tibia, and (ii) engage the femoral component, the tibial component having (i) bearing surfaces for directly engaging the condyles of the femoral component, and (ii) a second cutout or opening located between the bearing surfaces, a tibial insert removably mounted within the second cutout or opening of the tibial component by a second sliding rail and slot engagement, the second sliding rail and slot engagement including either elongated rails or elongated slots disposed on opposing sides of the tibial insert and extending in the anterior-posterior direction when the modular knee joint prosthesis is maintained in the extended position, and a post protruding from the tibial insert and an opening disposed on the femoral insert, wherein the post is configured to be positioned within the opening in both the extended and flexion positions, wherein the post protrudes from a concave surface formed on the tibial insert, and the opening is disposed on a convex surface formed on the femoral insert, wherein the concave surface is configured to be positioned against the convex surface in both the extended and flexion positions.

* * * * *